United States Patent [19]

Edwardson

[11] Patent Number: 4,984,985
[45] Date of Patent: Jan. 15, 1991

[54] DENTAL INSTRUMENT

[75] Inventor: Svante R. Edwardson, Solna, Sweden

[73] Assignee: Dentatus International AB, Hagersten, Sweden

[21] Appl. No.: 251,957

[22] Filed: Sep. 26, 1988

[51] Int. Cl.$^5$ .............................................. A61C 1/07
[52] U.S. Cl. ................................. 433/123; 433/118; 433/166
[58] Field of Search ............... 433/122, 123, 126, 127, 433/128, 165, 166, 118

[56] References Cited

U.S. PATENT DOCUMENTS

| 1,316,685 | 9/1919 | Cates | 433/123 |
| 2,411,234 | 11/1946 | Silver | 433/122 |
| 3,552,022 | 1/1971 | Axelsson . | |

FOREIGN PATENT DOCUMENTS

| 1123799 | 2/1962 | Fed. Rep. of Germany | 433/166 |
| WO83/00824 | 3/1983 | PCT Int'l Appl. | 433/166 |
| 30457 | of 1897 | United Kingdom | 433/122 |

OTHER PUBLICATIONS

"Smile", Science & Technology, Forbes, Jul. 25, 1988, pp. 190 and 192.

Primary Examiner—Cary E. Stone
Attorney, Agent, or Firm—Young & Thompson

[57] ABSTRACT

A motor driven dental instrument for peeling away a layer of a tooth is provided. The rotational movement of the driving shaft is transformed into an axially oscillating, not rotatable movement of a tool support of a working tool. The working tool is able to be placed in an angular position in relation to the tool support chosen by the dentist.

17 Claims, 4 Drawing Sheets

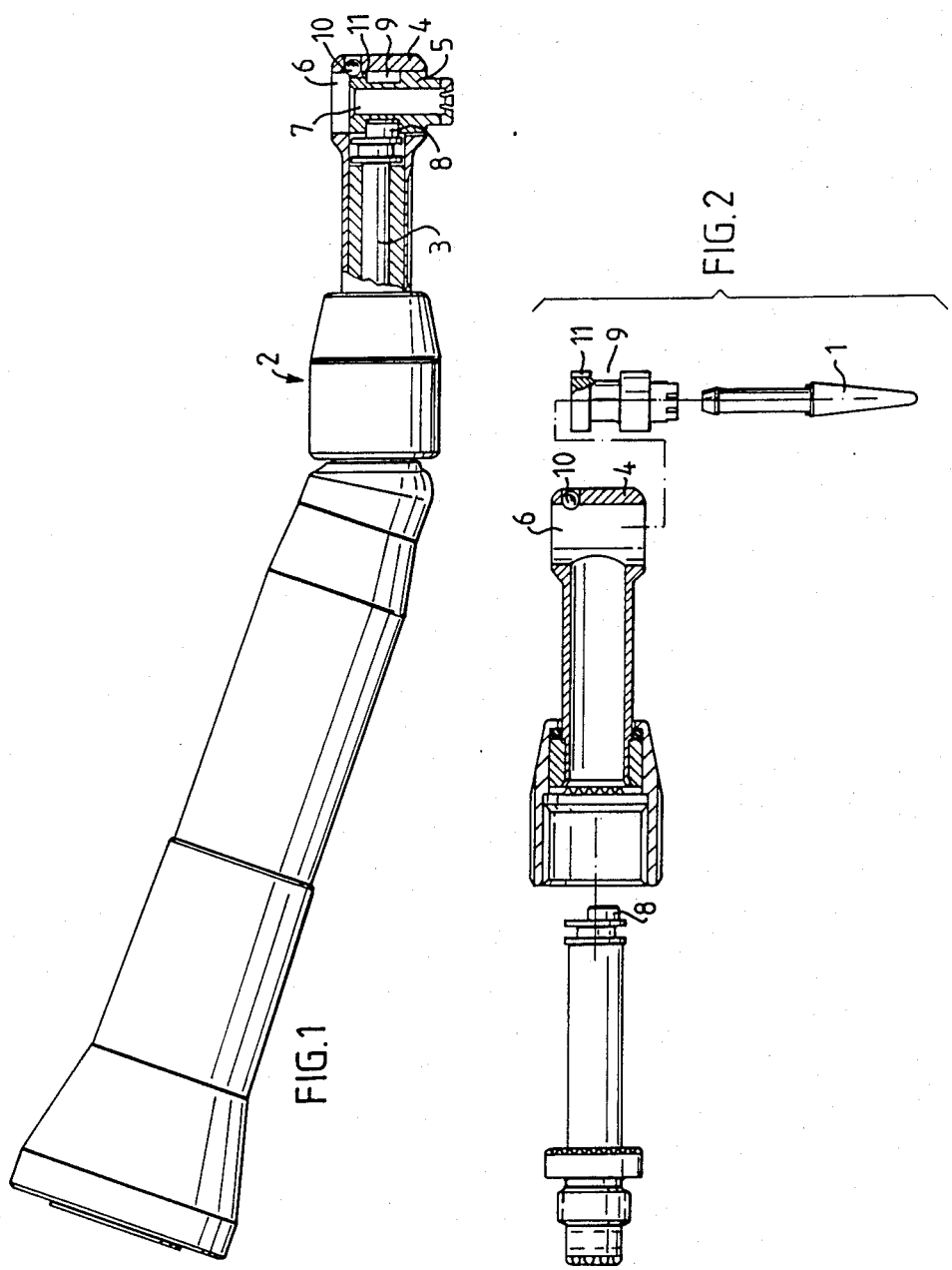

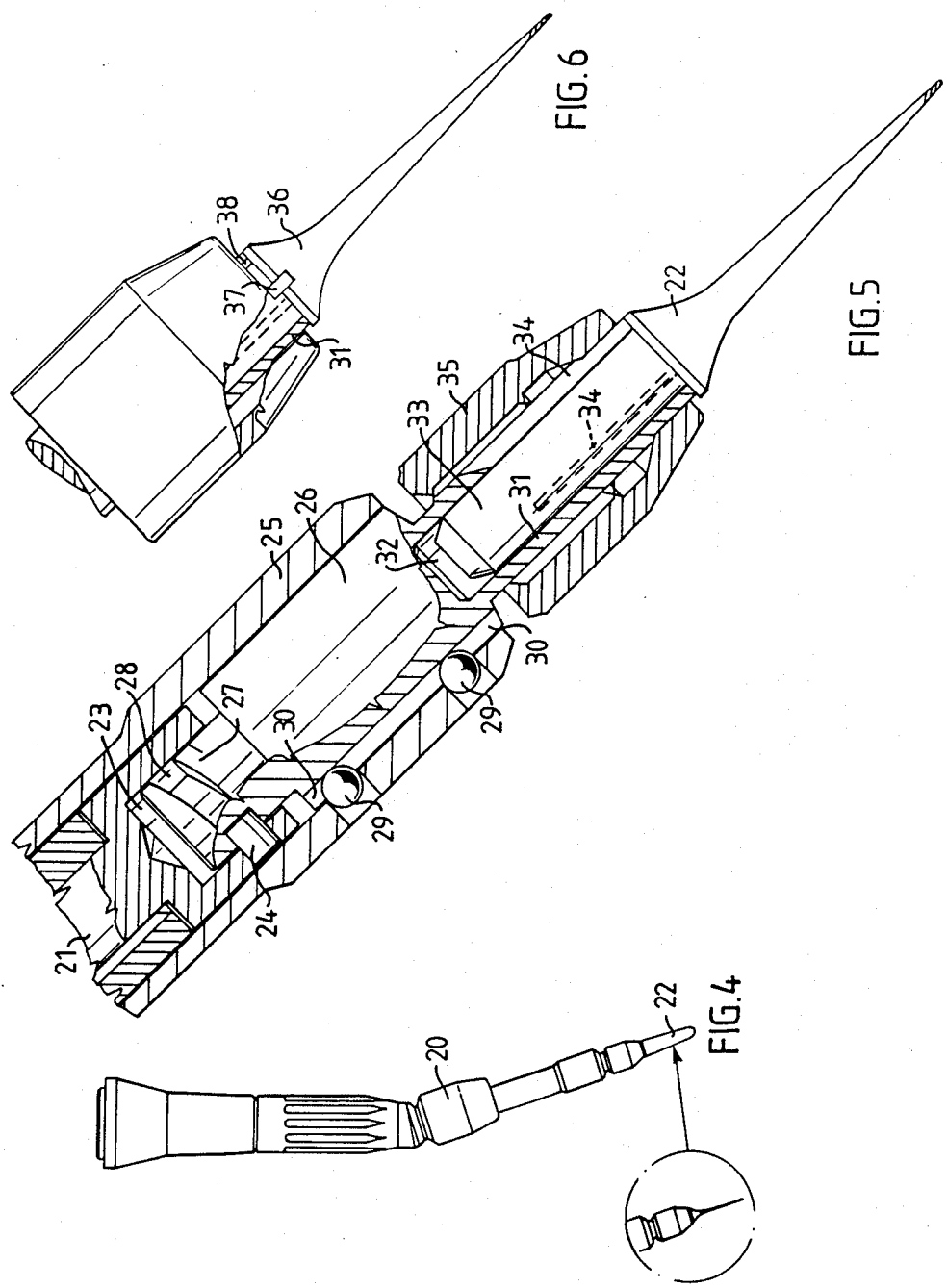

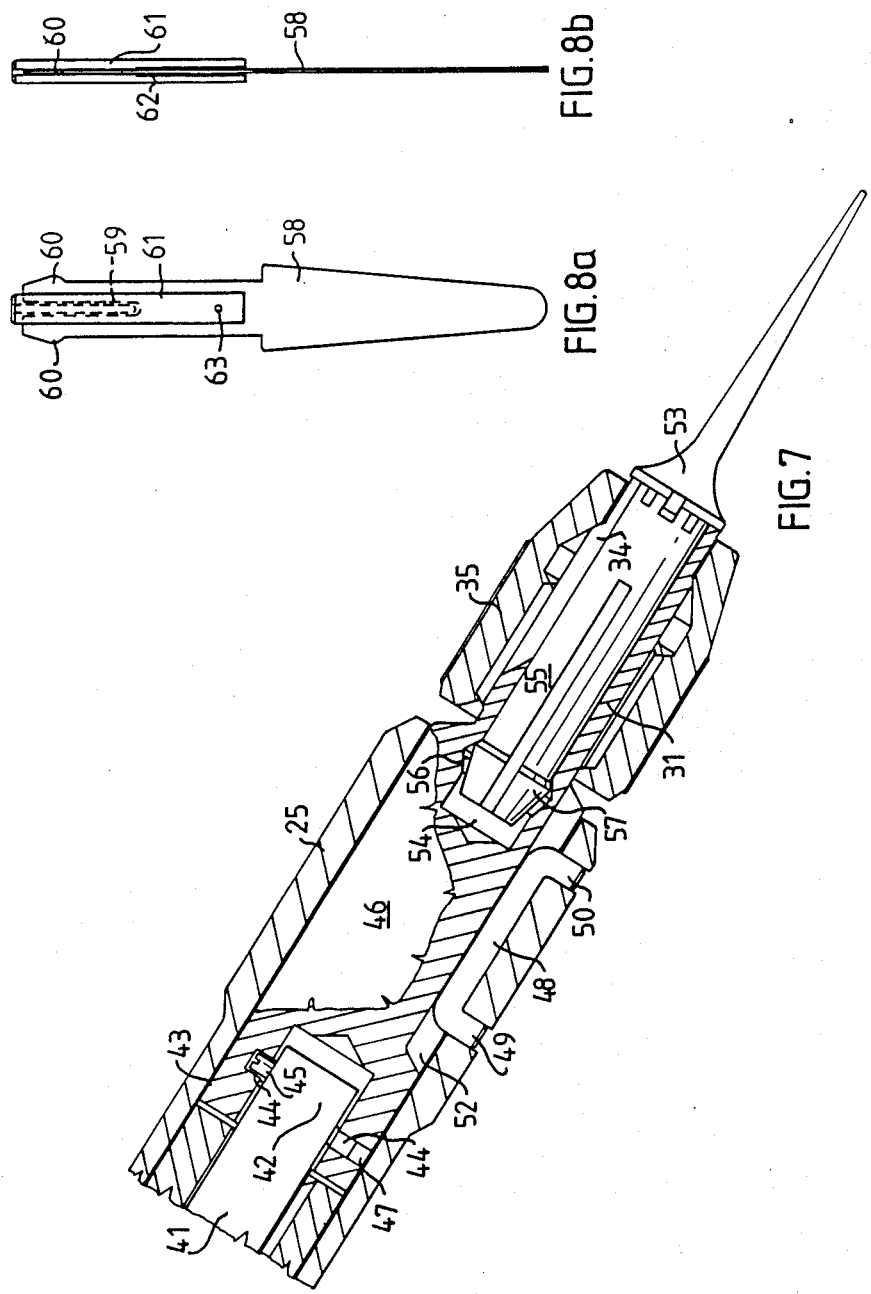

DENTAL INSTRUMENT

The present invention relates to a dental instrument and particularly to a motor driven device to peel away a thin layer of a tooth.

BACKGROUND OF THE INVENTION

In recent years it has been common to provide a thin laminate to the surface of one or more teeth, especially a white hard laminate to make yellowish teeth whiter but also in some cases to strengthen the teeth by providing them with a harder and stronger surface layer than they have naturally.

Every person is very sensitive for even very small anomalies of his teeth. Therefore, a hard laminate could not just be added to the teeth of a person. The laminate must have some thickness in order to stay adhered to the teeth for years and, sustain normal wear out. The laminate is often made of porcelain and is made at a dental laboratory and cemented to a tooth to be treated by the dentist. Therefore, a thin layer of the surface of the tooth ought to be peeled away as a start of the lamination procedure, a cast of the tooth is taken and sent to the dental laboratory where the porcelain laminate is made.

The object of the invention is to provide a dental instrument adapted for peeling away a thin surface layer of a wanted thickness and extension and to be easy to handle by the dentist making this kind of work.

The invention is based upon a prior instrument described in the U.S. Pat. No. 3,552,022 owned by the same applicant. Changes have been made in this instrument in order to have the feature aimed at above in order to make the inventive instrument.

A disadvantage with this prior endodontic treatment instrument, if it should be used as a peeling off instrument, is that the tool provided at the end of the instrument must not rotate but only oscillate in the axial direction of the tool, so that the dentist may control and check the position of the tool in a distinct way.

An object of the invention is therefore to provide a dental instrument having a working tool which is only oscillating in axial direction but not rotating.

Another object of the invention is to have the working tool changeable at will to different but wanted angular positions around its axis. It could be an advantage for the dentist to use the same kind of spatula-shaped tool as in the U.S. Pat. No. 3,552,022 mentioned above but to be able to place it in different angular positions at will dependent upon the actual work he is doing at the tooth under process, because then he could use the same tool during the whole processing work of a tooth.

A still further and very important object of the invention is to provide a comfortable working position for the hand of the dentist during the peeling work, in which the tip of the tool should be moved over the whole surface of the tooth under treatment.

A still further object of the invention is to provide an instrument which may use tools on the market for which no or only minor changes have to be made in order to keep the expenses for the instrument down.

DISCLOSURE OF THE INVENTION

The object invention is a dental instrument for peeling away a tooth surface layer including:
(a) a tool support,
(b) a tool having a tip with a rough surface,
(c) rotational drive means,
(d) means connected to said rotational drive means for producing alternating movement forces, in the direction of the axis of said tool support,
(e) means for preventing said tool support from rotating,
(f) means for holding said tool in said tool support in a chosen angular position in relation to said tool support.

Preferably the tool has a working part the tip of which is not rotationally symmetrical, for instance being spatula-formed, and the tool holding means is able to hold the tool in an angular position chosen among a limited number of predetermined positions.

In a preferred embodiment of the instrument according to the invention the axes of said tool support and said tool are extending in the same direction as the axis of said rotational drive means.

Further objects and features of the invention will be fully understood from the following detailed description with reference to the accompanying drawings.

BRIEF DESCRIPTION OF THE DRAWINGS

FIG. 1 shows a side view, partly in section, of a first embodiment of the dental instrument according to the invention mounted on a rotational driving unit;

FIG. 2 is an exploded view, partly in section, of the front part of the device shown in FIG. 1;

FIG. 4 shows a side view of a second, preferred, embodiment of the dental instrument according to the invention showing the instrument tool in two different angular positions (one encircled);

FIG. 5 shows an enlarged sectional view of the front part of the instrument shown in FIG. 4 including the movement transducing means;

FIG. 6 shows a side view, partly in section, of the outermost front part of a modification of the embodiment shown in FIG. 4;

FIG. 7 shows a modification of the embodiment shown in FIG. 5; and

FIGS. 8a and 8b show two side views from two sides 90° apart.

DESCRIPTION OF THE PREFERRED EMBODIMENTS

Figure 3C:
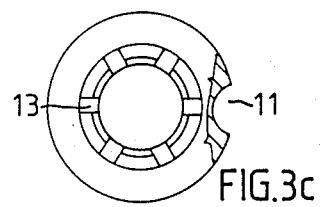
FIG. 3c shows a bottom view of the tool support means, partly in section, relating to IIIc in FIG. 3b.
Figure 3A:
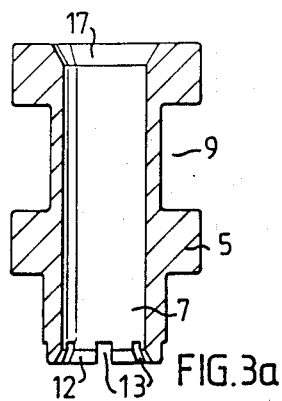
FIGS. 3a and 3b show a sectional view and a side view, partly in section, respectively, of an embodiment of a tool support means.
Figure 3B:
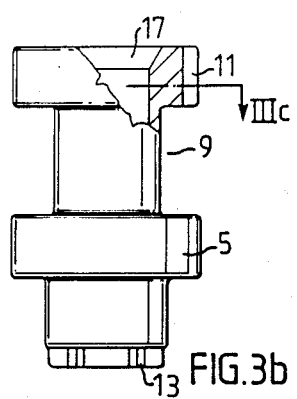
Figure 3D:
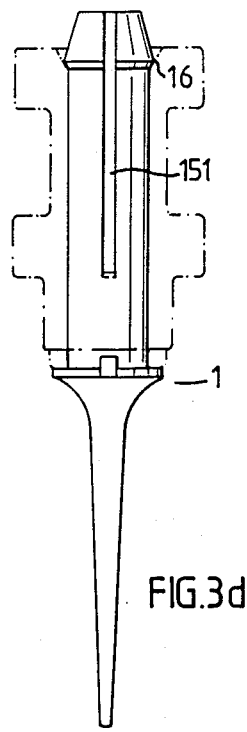
FIGS. 3d and 3e show two side views of a tool to be inserted in the tool support means, the tool support means being shown in dashed lines in FIG. 3d to illustrate the tool also in an inserted position.

With reference to the embodiment in FIGS. 1, 2 and 3a to 3e, the apparatus for holding and driving a dental instrument tool, such as an elongated wedgeshaped tip commonly used for prophylactic smoothing, polishing and removal of amalgam overhangs, during its operation comprises a slim generally cylindric handle 2 having a design general in the art. Said handle 2 houses a rotary shaft 3 which is driven by a motor (not shown) via a connection (not shown), as in dental hand pieces. Preferably the handle belongs to an already existing dental driving equipment, and merely an exchangeable end portion of the handle is designed according to the invention.

The handle ends with a cylindrical sleeve 4 set at right angles thereto and extending slightly therefrom at both sides. A piston-like socket 5 fits into a cylindrical bore 6 of the sleeve 4 and is guided thereby in a rectilinear path perpendicular to the length direction of the end of the handle 2. A central cylindrical bore 7 in the socket 5 is of a size suitable for inserting the shaft end portion of the tool 1 therein and for retaining the same with frictional engagement. The shaft 3 ends with an eccentric pin 8 which protrudes past the cylindrical face 6 and into a circumferential groove 9 cut in the socket 5. When the shaft 3 is turned, the pin 8 reciprocates the socket 5, and the tool 1 inserted therein, in their length direction, i.e. at right angles to the length direction of the handle. The eccentricity of the pin 8 is so great that the amplitude of the stroke is of the order of 1 to 2 millimeters, and the frequency may be preferably 6,000 to 10,000 strokes per minute.

In accordance with the invention and in contrary to the apparatus according to U.S. Pat. No. 3,552,022 the socket is not turnable around its axis and the tool 1 is not turnable around its axis in the socket.

In order to prevent the socket from turning the inner wall of the sleeve 4 is provided with a protrusion, which in the embodiment shown is a sphere 10 mounted in a through bore in the upper part of the sleeve 4, just opposite the upper part of the socket 5 above the groove 9 at the end turned from the tool 1. The socket is provided with a canal 11 for the for the protrusion 10 in the sleeve 4, which canal 11 in the embodiment shown has a rounded form adapted to accommodate to the rounded form of the protruding part of the sphere.

In order to prevent the tool from turning in the socket 5 the end of the socket bore 7 widens at its bottom part turned to the tool and is at the widened part 12 (see FIG. 3a) provided with a number of through canals 13 having open bottom ends. The tool 1, which in the shown embodiment is a modification of a diamond tip sold by Dentatus under the name EVA-22, is provided with at least one nib 14 provided at the base of the tool shaft 15 and adapted to be inserted in one of the canals 13 at insertion of the tool shaft 15 into the socket 5. Preferably, there are two nibs placed diametrically opposite to each other and the number of canals 13 is even, for instance, six. Because of the number of canals the dentist is able to place the tool 1 in the very one of a number of different angular positions appropriate for the actual work at the tooth to be treated.

As mentioned above the shaft portion 15 of the tool is retained in the socket bore 7 by friction engagement. In order to make the retainment still more secure a deep axially extending diametric through slit is cut from the shaft end to a depth of approximately ¾ of the shaft length. Near the shaft end the shaft is slightly widened by a protruding part 16. The socket bore 7 has a widened part 17 at its upper end turned from the tool 1 and the tool shaft 15 has a length to permit the widened part 16 to snap into the widened bore part 17 when the tool has been properly inserted having the two nibs 14 resting in two canals 13. A central through cut 151 is made in the shaft 15 from its outer end to about ¾ of its length in order to make it possible for the shaft to pass through the canal 7. The material of the tool shaft is quite stiff and only slightly resilient and thus the tool will be held firmly until the dentist presses at the back of the tool 1, for instance by using a special press tool (not shown) or by pressing the back of the sleeve 4 with the protruding back of the shaft 15 towards a table surface or the like.

In working with the fronts of the teeth it is sometimes uncomfortable to use the angularly deflecting position of the tool on a dental handle shown in the embodiments in FIGS. 1 to 3, commonly used in motor driven dental instruments. Since a thin layer of a tooth to be treated shall be taken away and it is a wish to have this layer as even and as determinable as possible, it is essential that the dentist uses an instrument which works more like an extension of his hand than an angularly deflected tool may do.

Therefore, the embodiments shown in FIGS. 4 to 7 represent an advantageous further development of the invention, the embodiment of the invention shown in FIG. 6 together with the movement transformation part shown in FIG. 5 being the preferred one.

Referring to FIGS. 4 and 5 a dental instrument handle 20 houses a rotary shaft 21 as in the embodiment shown in FIGS. 1 to 3. In the embodiment in FIGS. 4 and 5 a tool 22, which in this embodiment may be the diamond tip sold by Dentatus under the name EVA-22 mentioned above without modifications, is provided at the end of the instrument having its axis along the extension of the axis of the shaft 21.

In order to provide the oscillations in axial direction of the tool 22 at rotation of the shaft 21 the shaft has a widened part in its end provided with a central cylindrical bore 23 in its end. A protrusion, for instance provided by a cylindrical pin 24 firmly attached in a hole in the shaft wall, is projecting into the side of the bore 23 at about ⅓ of its depth.

The shaft 21 is surrounded by a cylindrical housing 25 having the form of its central bore adapted to the outer form of the shaft 21. The front end of the housing 25 is extending beyond the end of the shaft 21. A rotationally symmetrical tool support piece 26 being locked against rotation, is inserted at about half of its length in the extending end of the housing. The inserted part of the tool support piece 26 has approximately the same diameter as the widened part of the shaft 21 and has an end part 27 having a diameter adapted to the inner diameter of the bore 23. The end part 27 is provided with a circumferential groove 28 which is tapered in such a way that it has diametrically opposite parts lying on mutually different axial levels. When the shaft 21 rotates the tool support 26 is oscillating in its axial direction as the pin 24 is moved around the end part 27 of the piece 26 in the tapered groove 28.

The pin 24 may be removable at service of the instrument and also its projection length may be adjustable by having the hole, in which the pin is seated, and the pin 24 threaded. Another way to have the pin removable at service is to have a hole (not shown) in the groove 28 into the center of the end part 27 at one angular position for the shaft in relation to the part 27 such that the shaft may be placed in a position having the pin seated opposite the hole and the pin 24 be pushed into the hole in the groove so that the support piece can be removed from the shaft 21. However, it is not absolutely necessary to have this removal opportunity at service and then the pin 24 may just be tightly fitted.

Rotation of the piece 26 is prevented by a stop device 29 protruding into the inside of the housing 25 and into an axially extending groove 30 in the side of the support 26. In the embodiment shown the stop device consists of spheres 29 inserted in holes in the housing walls and protruding into the groove 30 in a similar way as the sphere 10 in FIG. 1 is protruding into the groove 11.

The front part 31 of the tool support 26 extending out from the housing 26 has a smaller diameter than the part inside the housing and has a deep central boring 32 adapted to receive the shaft end 33 of the tool 22 and to retain the same with frictional engagement. A number of axially extending through cuts 34 are made in the wall of the front part 31 and the outermost outer end of it is threaded. A cylindrical chuck sleeve 35 surrounds the front part 31 and has an inner threaded front part adapted to the outer threaded end of the part 31. The design of the chuck unit 31, 32, 34, 35 to hold and to lock an inserted tool is well known in the art and need no further description and explanation.

In the embodiment according to FIGS. 4 and 5 the tool 22 can be fixed in whichever angular position around its axis the dentist chooses to put it in. However, the tool 22 is rather small and it may be advantageous for the dentist to be able to put the tool only in a limited number of angular positions in order to put the tool in exactly the same angular positions from time to time. Therefore, as shown in FIG. 6, the tool 36 may be provided with at least one, preferably two, nib 37 at the base of its shaft part and the outer end of the front part 31 of the tool support with a number of recesses 38 to engage the nibs in the same way as is shown in FIGS. 1 to 3.

As shown in FIG. 7, the arrangement to transfer the rotational movement of the shaft 41 to an oscillating movement of the tool support 46 may consist of a central part 42 of the shaft being surrounded by a ring-formed end part 43 of the tool support 46. A tapered, encircling groove 44 is provided at the inside of the part 43. A protrusion 45, preferably in the form of a threaded screw without screw head, is provided on the outside of the shaft part 42. A through hole 47 connected to the groove 44 may be made in the wall of the part 43 in order to make it possible to screw out the protrusion at service of the instrument.

FIG. 7 also shows a rotation preventing arrangement for the tool support 46 consisting of a cylindrical pin 48 having its ends 49,50 bent 90° and inserted from the inside into two holes in the wall of the housing 25. The straight part of the pin 48 is projecting in an axially extending canal 52 in the tool support 46.

Figure 3E:
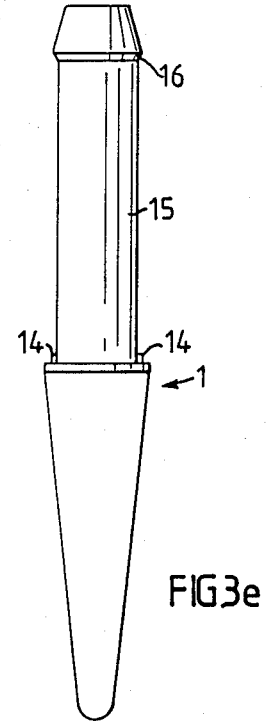

Further, FIG. 7 shows a tool 53 having the same design as the tool 1 shown in FIG. 3e. The depth of the centrol bore 54 in the front part 31 is adapted to have the shaft 55 of the tool 53 inserted and has a wider part 56 adapted for the protruding part 57 of the shaft 55 to snap into.

FIGS. 8a and 8b show two side views of another embodiment of the tool 58, which is merely stamped out of a sheet of metal. A central cut 59 having a rounded bottom is made in the shaft. Protrusions 60 are provided near the outer end of the shaft in order to be snapped into the widened sections 17 (e.g. shown in FIG. 3a) or 56 (shown in FIG. 7). The embodiment shown in FIGS. 8a and 8b may thus replace the tools 1 and 53.

A flat little tool may be difficult for the dentist to grab, if he has put it on a table or the like. Tools of the kind mentioned above sold by Dentatus under the name of EVA are usually marked with a colour to indicate the grain size of the diamond-coated tool tip. According to an embodiment of the invention, the colour marking of the flat tool shown in FIGS. 8a and 8b is made by a separately applicable loose device 61, preferably of plastic material and preferably cylindrical. The device 61 may have the appropriate colour, a diameter larger than the width of the central cut 59 in the tool shaft but shorter than the width of the shaft, axially extending, diametrically opposing lateral cuts are made along its whole length leaving a material bridge between the cuts adapted to make the center of the cylinder insertable into the cut 59 of the tool 58 leaving a play to the lateral walls of the cut in order not to disturb the lateral movement of the legs having the protrusions 60, during the insertion or withdrawal operation of the tool. In its front end intended to be turned to the tip of the tool 58, an axial through-cut 62 is made in the marking device 61 mating with its lateral cuts and extending to about 1/5 to ⅕ of its length. When the marking device 61 is applied on the tool 58, the part having the through-cut 62 is extending over the material of the tool shaft. Preferably the tool shaft, and possibly also the marking device 61, have a through-hole 63 in this area adaptable for letting material of the plastic material of the device passing through the shaft hole to make a material bridge through the hole of a warming or stamping operation or the like in the hole area after mounting the device 61 on the tool shaft in order to have it secured to the shaft. The length of the cylinder is preferably such that a little part of it is protruding on the rear end of the tool shaft. The colour marking device 61 may also take some other outer form than a cylinder, the main thing is that it is a colour marking, plastic device placed in the cut 59, having parts protruding out from both sides of the tool shaft and being held in place on the shaft.

While there has been shown and described what is considered at present to be the preferred embodiment of the present invention, it will be appreciated by those skilled in the art that modifications of such embodiment may be made. It is therefore desired that the invention not be limited to these embodiments, and it is intended to cover in the appended claims all such modifications as fall within the true spirit and scope of the invention.

We claim:

1. A dental instrument for peeling away an outer layer of tooth surface layer including:
    (a) a tool support,
    (b) a tool having a tip with a rough surface and having sufficient rigidity to peel away a thin layer of tooth surface,
    (c) rotational drive means,
    (d) means in continuous engagement with said rotational drive means transforming its rotary movement into alternating movement forces in the direction of the axis of said tool support,
    (e) means for preventing said tool support from rotating, and
    (f) means for holding said tool in said tool support in a chosen angular position in relation to said tool support,
    wherein said means for holding said tool in said tool support is able to hold said tool in an angular position chosen among a limited number of predetermined positions, and
    wherein said holding means includes at least one nib at the base of a rotational symmetric shaft of said tool to be inserted into said support and a number of recesses around the entrance end of said support adapted to accommodate said at least one nib when said tool is inserted.

2. A dental instrument according to claim 1, wherein said tool has a working part which is spatula-shaped.

3. A dental instrument according to claim 1, wherein the axes of said tool support and said tool are extending in the same direction as the axis of said rotational drive means.

4. A dental instrument according to claim 3, wherein said movement transforming means includes a first transformer part situated on the rotating end of said rotational drive means and a second transformer part situated on said tool support, one of said transformer parts surrounding the other, and the second transformer part being provided with a ringformed encircling groove having its opening turned towards said first part and being tapered such that said groove has diametrically opposite parts lying on mutually different axial levels, and the first transformer part having a protrusion protruding into said groove.

5. A dental instrument according to claim 3, wherein said means for holding said tool in said tool support is able to hold said tool in an angular position chosen among a limited number of predetermined positions.

6. A dental instrument according to claim 3, wherein said tool has a working part which is spatula-shaped.

7. A dental instrument according to claim 3, wherein said tool holding means includes a chuck.

8. A dental instrument according to claim 3, wherein said tool is a spatula shaped tip of a kind known per se commonly used for smoothing, polishing and removal of amalgam overhangs.

9. A dental instrument according to claim 8, wherein said tool holding means includes a chuck having a number of recesses around the entrance of an opening to receive said tool and that said tool is provided with at least one nib adapted to be received in one of said recesses and situated at the base of a shaft of said tool.

10. A dental tool for a dental instrument giving a reciprocating movement to said tool, said tool having a flat spatula-shaped working part formed integrally with a straight shaft having a through control slit going from its outer end and extending into a part of its length to divide the shaft end into two legs being resiliently bendable towards each other, wherein each leg is provided with a radially outwardly projecting part near its end.

11. A dental tool according to claim 10, wherein at least one nib is provided at the base of said shaft adjacent to said working part.

12. A dental tool according to claim 11, wherein said at least one nib comprises two nibs disposed diametrically opposite one another at the base of said shaft adjacent said working part.

13. A dental tool according to claim 10, wherein said shaft is flat having said slit in the middle of its long sides.

14. A dental tool according to claim 13, further comprising a separately applicable device inserted in said slit and having parts projecting from the surface of said tool shaft on both sides and being held in place in said slit by having at least one lateral cut at its insertion location.

15. A dental tool according to claim 10, wherein said shaft is cylindrical.

16. A dental instrument for peeling away an outer layer of tooth surface layer including:

(a) a tool support,
(b) a tool having a tip with a rough surface and having sufficient rigidity to peel away a thin layer of tooth surface,
(c) rotational drive means,
(d) means in continuous engagement with said rotational drive means transforming its rotary movement into alternating movement forces in the direction of the axis of said tool support,
(e) means for preventing said tool support from rotating, and
(f) means for holding said tool in said tool support in a chosen angular position in relation to said tool support, wherein the axes of said tool support and said tool are extending in the same direction as the axis of said rotational drive means, and wherein said movement transforming means includes a first transformer part situated on the rotating end of said rotational drive means and a second transformer part situated on said tool support, one of said transformer parts surrounding the other, and the second transformer part being provided with a ringformed encircling groove having its opening turned towards said first part and being tapered such that said groove has diametrically opposite parts lying on mutually different axial levels, and the first transformer part having a protrusion protruding into said groove.

17. A dental instrument for peeling away an outer layer of tooth surface layer including:

(a) a tool support,
(b) a tool having a tip with a rough surface and having sufficient rigidity to peel away a thin layer of tooth surface,
(c) rotational drive means,
(d) means in continuous engagement with said rotational drive means transforming its rotary movement into alternating movement forces in the direction of the axis of said tool support,
(e) means for preventing said tool support from rotating, and
(f) means for holding said tool in said tool support in a chosen angular position in relation to said tool support, wherein the axes of said tool support and said tool are extending in the same direction as the axis of said rotational drive means, wherein said tool is a spatula-shaped tip adapted for smoothing, polishing and removal of amalgam overhangs, and wherein said tool holding means includes a chuck having a number of recesses around the entrance of an opening to receive said tool and that said tool is provided with at least one nib adapted to be received in one of said recesses and situated at the base of a shaft of said tool.

* * * * *